(12) United States Patent
Murad et al.

(10) Patent No.: US 8,839,957 B2
(45) Date of Patent: Sep. 23, 2014

(54) PROSTHETIC HEART VALVE PACKAGING SYSTEM

(76) Inventors: Michael C. Murad, Corona, CA (US);
Mark Van Nest, Aliso Viejo, CA (US);
Jackie Lau, Anaheim, CA (US)

(*) Notice: Subject to any disclaimer, the term of this patent is extended or adjusted under 35 U.S.C. 154(b) by 232 days.

(21) Appl. No.: 13/026,841

(22) Filed: Feb. 14, 2011

(65) Prior Publication Data

US 2011/0198244 A1    Aug. 18, 2011

Related U.S. Application Data

(60) Provisional application No. 61/304,722, filed on Feb. 15, 2010.

(51) Int. Cl.
*B65D 85/30* (2006.01)
*A61F 2/24* (2006.01)
*A61F 2/00* (2006.01)

(52) U.S. Cl.
CPC *A61F 2/0095* (2013.01); *A61F 2/24* (2013.01)
USPC .............................. 206/438; 206/363; 623/2.1

(58) Field of Classification Search
CPC .................................. A61F 2/0095; A61F 2/24
USPC .......... 206/210, 363, 438; 623/2.1, 2.11, 2.17
See application file for complete search history.

(56) References Cited

U.S. PATENT DOCUMENTS

| | | | |
|---|---|---|---|
| 4,101,031 A | 7/1978 | Cromie | |
| 4,182,446 A | 1/1980 | Penny | |
| 4,211,325 A * | 7/1980 | Wright | 206/438 |
| 4,697,703 A | 10/1987 | Will | |
| 4,801,015 A | 1/1989 | Lubock et al. | |
| 5,167,223 A | 12/1992 | Koros et al. | |
| 5,236,450 A | 8/1993 | Scott | |
| 5,480,425 A | 1/1996 | Ogilive | |
| 5,531,785 A | 7/1996 | Love et al. | |
| 5,560,487 A | 10/1996 | Starr | |
| 5,578,076 A | 11/1996 | Krueger et al. | |
| 5,582,607 A | 12/1996 | Lackman | |
| 5,615,770 A | 4/1997 | Applebaum et al. | |
| 5,690,226 A | 11/1997 | N'Guyen | |
| 5,720,391 A | 2/1998 | Dohm et al. | |
| 5,776,187 A | 7/1998 | Krueger et al. | |
| 5,800,531 A | 9/1998 | Cosgrove et al. | |
| 5,823,342 A * | 10/1998 | Caudillo et al. | 206/438 |
| 5,868,253 A | 2/1999 | Krueger et al. | |
| 5,980,569 A | 11/1999 | Scirica | |
| 5,984,959 A | 11/1999 | Robertson et al. | |
| 6,090,138 A * | 7/2000 | Chasak et al. | 606/1 |
| 6,126,007 A * | 10/2000 | Kari et al. | 206/438 |
| 6,197,053 B1 | 3/2001 | Cosgrove et al. | |

(Continued)

OTHER PUBLICATIONS

International Search Report from corresponding international application No. PCT/US2011/024904 dated Oct. 25, 2011.

*Primary Examiner* — Luan K Bui
(74) *Attorney, Agent, or Firm* — AnneMarie Kaiser; Guy Cumberbatch

(57) ABSTRACT

Packaging for prosthetic heart valves including an assembly for securely retaining a heart valve within a sterile jar and facilitating retrieval therefrom. The assembly includes a packaging sleeve that fits closely within the jar and has a clip structure for securing a valve holder. A delivery handle on the end of a shaft couples with the valve holder while the packaging sleeve engages the jar to prevent rotation. The assembly of the packaging sleeve, valve, and holder can then easily be removed from the jar.

12 Claims, 9 Drawing Sheets

(56) References Cited

U.S. PATENT DOCUMENTS

| | | | |
|---|---|---|---|
| 6,199,696 B1 * | 3/2001 | Lytle et al. | 206/438 |
| 6,346,094 B2 * | 2/2002 | West et al. | 206/365 |
| 6,416,547 B1 * | 7/2002 | Erickson et al. | 623/2.11 |
| 6,534,004 B2 | 3/2003 | Chen et al. | |
| 6,591,998 B2 | 7/2003 | Haynes et al. | |
| 6,723,122 B2 | 4/2004 | Yang et al. | |
| 6,736,845 B2 | 5/2004 | Marquez et al. | |
| 6,966,925 B2 | 11/2005 | Stobie | |
| 7,389,874 B2 * | 6/2008 | Quest et al. | 206/438 |
| 7,699,168 B2 * | 4/2010 | Ryan et al. | 206/438 |
| 7,712,606 B2 | 5/2010 | Salahieh et al. | |
| 2002/0120328 A1 | 8/2002 | Pathak et al. | |
| 2006/0195183 A1 | 8/2006 | Navia et al. | |
| 2009/0130162 A2 | 5/2009 | Pathak et al. | |
| 2009/0164005 A1 | 6/2009 | Dove et al. | |
| 2011/0147251 A1 * | 6/2011 | Hodshon et al. | 206/438 |

\* cited by examiner

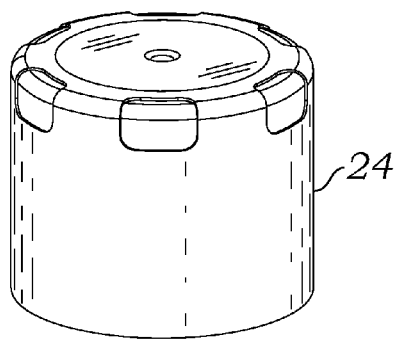
Fig.1
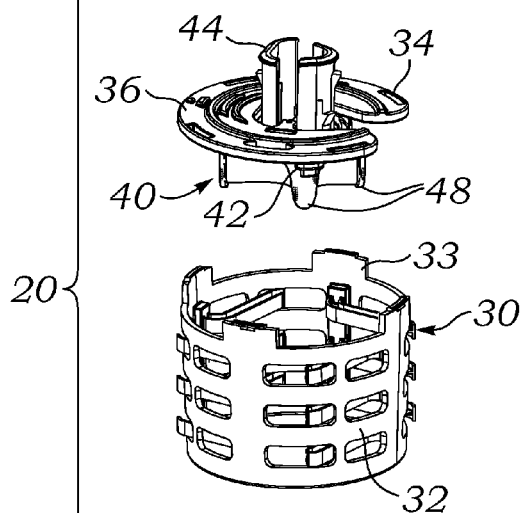
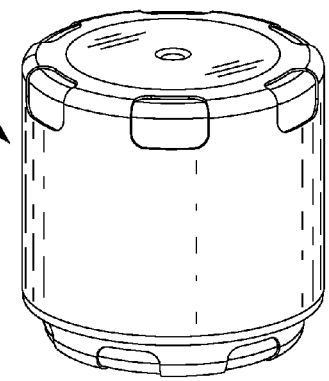
Fig.2
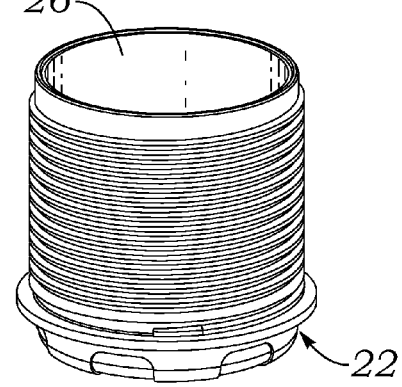
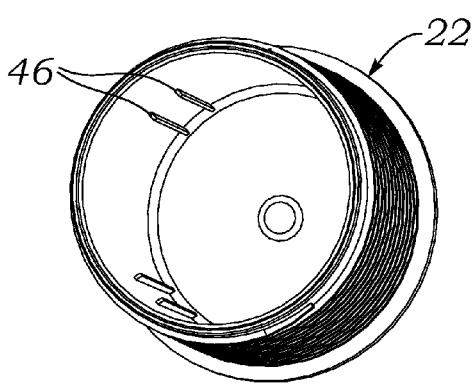
Fig.3

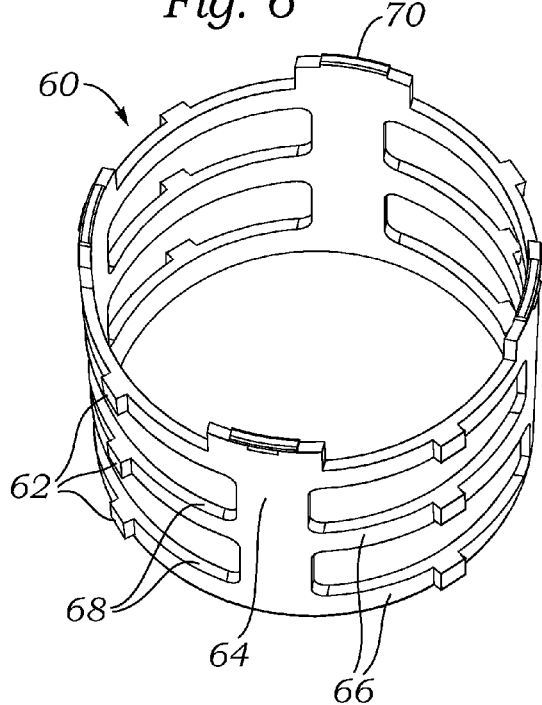
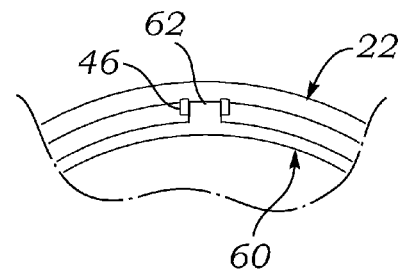
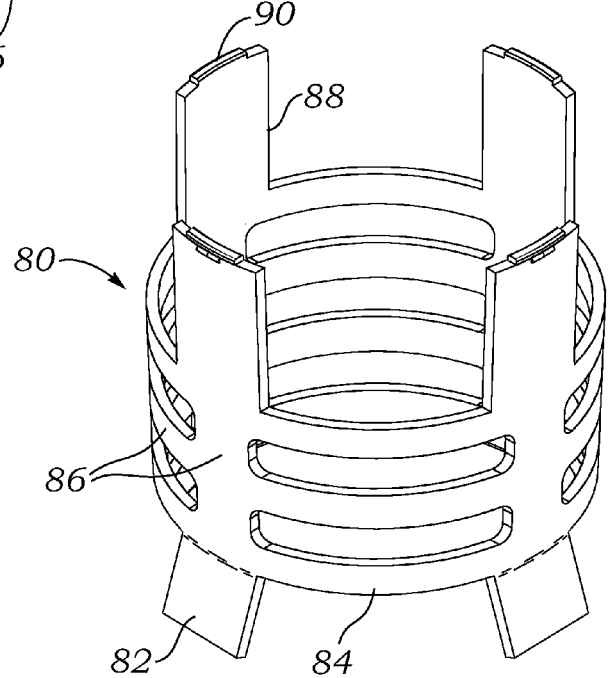

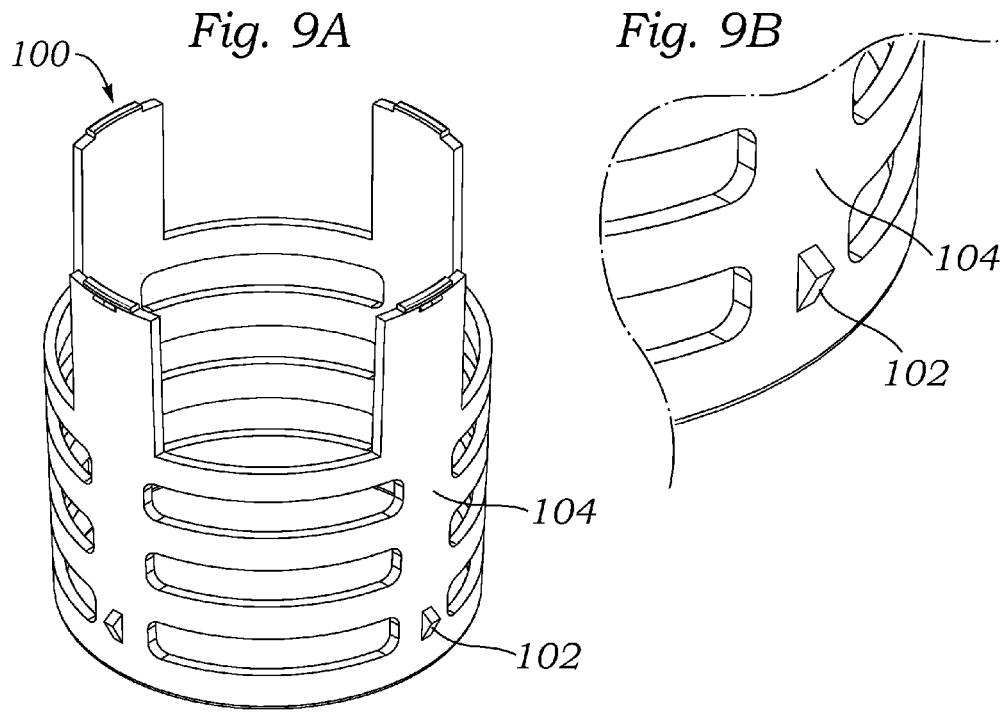
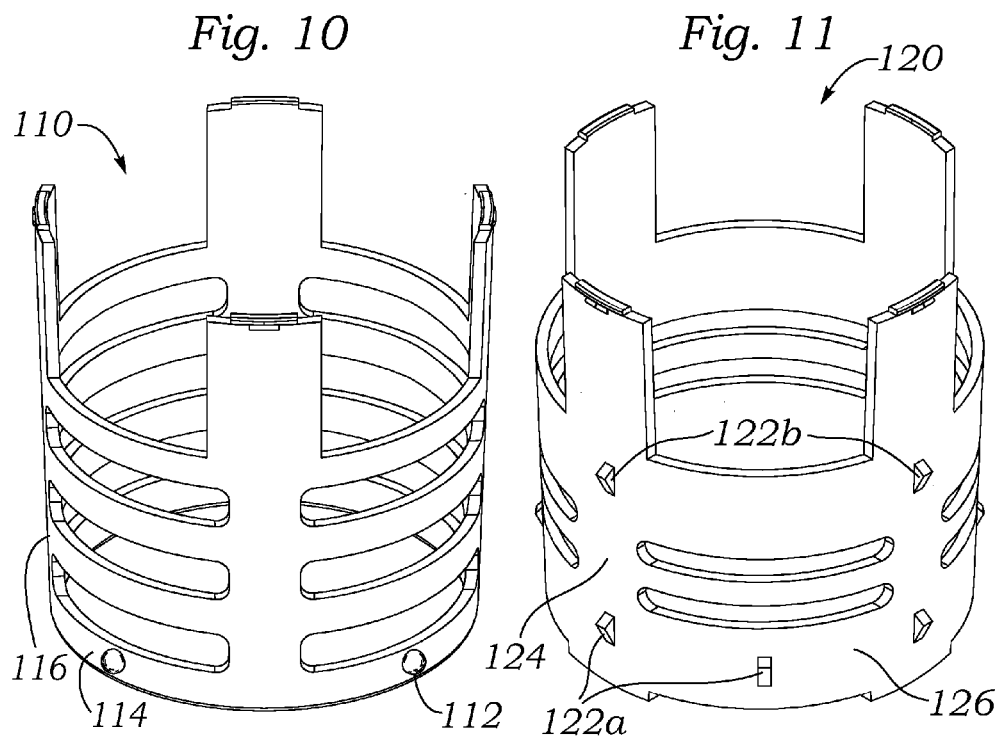

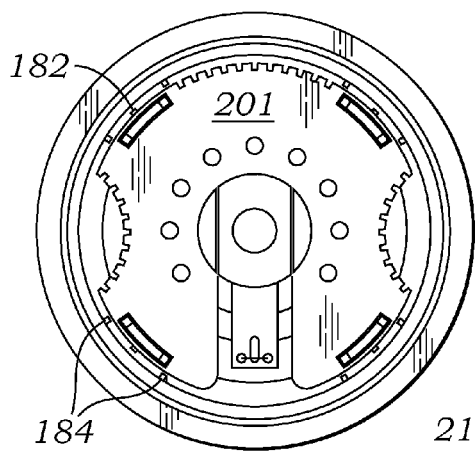
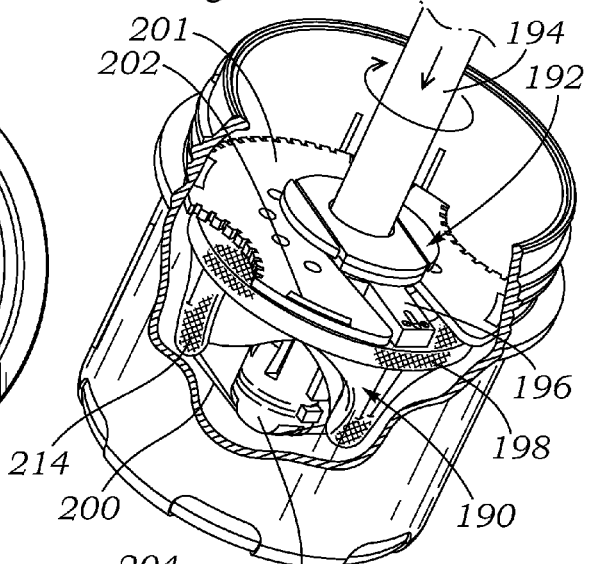
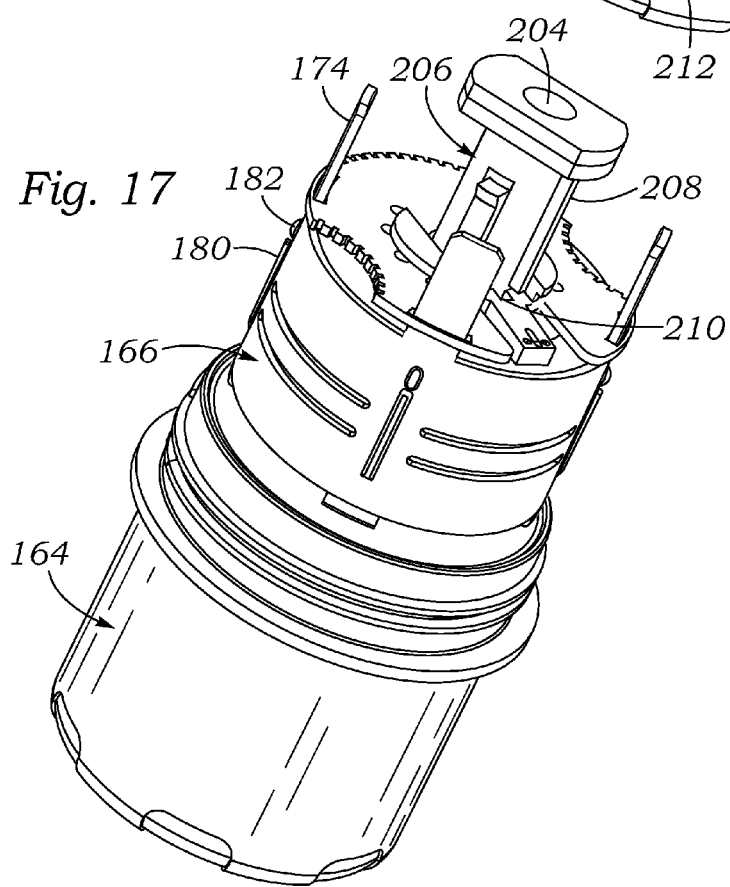

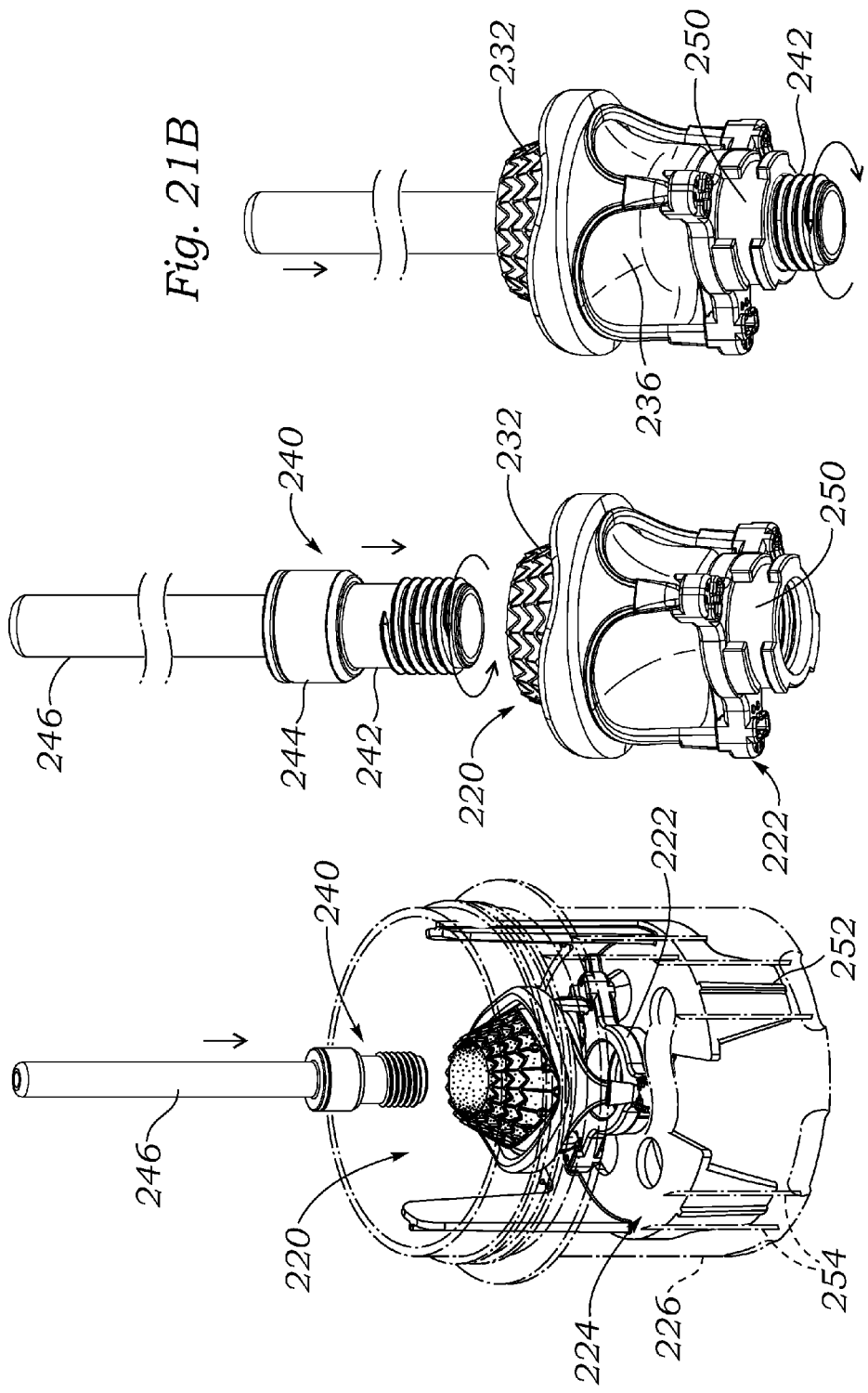

PROSTHETIC HEART VALVE PACKAGING SYSTEM

RELATED APPLICATIONS

The present application claims priority under 35 U.S.C. §119(e) to U.S. provisional application No. 61/304,722 filed Feb. 15, 2010.

FIELD OF THE INVENTION

The present invention generally relates to packaging for prosthetic heart valves and, more particularly, to an assembly for securely retaining a heart valve within a sterile jar and facilitating retrieval therefrom.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually, and about one-half of these patients received mechanical heart valves, which are composed of rigid, synthetic materials. The remaining patients received bioprosthetic heart valve replacements, which utilize biologically derived tissues for flexible fluid-occluding leaflets.

The most successful bioprosthetic materials for flexible leaflets are whole porcine valves and separate leaflets made from bovine pericardium stitched together to form a tri-leaflet valve. However, flexible leaflets formed of polymeric, fiber-reinforced, and other synthetic materials have also been proposed. The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

Bioprosthetic heart valves are packaged in jars filled with preserving solution for shipping and storage prior to use in the operating theater. To minimize the possibility of damage to the relatively delicate bioprosthetic heart valves, they are stabilized with bracketing structure to prevent them from striking the inside of the jar. The valves are stabilized with various structures, including a 2- or 3-piece clip and tubular sleeve structure, such as shown in U.S. Pat. No. 6,416,547 to Erickson, et al.

Prosthetic valves typically have a valve holder centrally located and sutured thereto, and the holders are attached to the inflow sewing ring for mitral valves and to the inflow cusps or outflow commissure tips for aortic valves. A delivery handle usually couples to the valve holder while still in the jar and lifts the valve assembly out of the jar. The valve may be removed from the jar using the handle and rinsed in a shower or immersed and agitated in a bath to remove residual preservative solution.

Despite a number of choices, there is still a need in the art for alternative packaging for heart valves that enables a medical practitioner to easily remove the valve using a surgical handle.

SUMMARY OF THE INVENTION

The present application provides a packaging assembly for prosthetic heart valves that includes a jar having an open end and a closed bottom, and a plurality of inwardly-directed rails circumferentially distributed around the jar interior. A prosthetic heart valve having an inflow end and an outflow end attaches to a valve holder. A packaging sleeve sized to fit closely within the jar includes structure to which the valve holder removably couples so that the heart valve is restrained from gross movement within the jar. The sleeve further includes a plurality of protrusions circumferentially distributed around a sleeve periphery, wherein an exterior diameter defined by the protrusions is larger than the inner diameter defined by the rails so as to create an anti-rotation interference between the sleeve and the jar to limit rotation of the sleeve while in the jar.

In the assembly described above, the plurality of protrusions are preferably evenly circumferentially distributed around the sleeve periphery, and there are two inwardly-directed rails on the jar for every protrusion on the sleeve so that each protrusion may be flanked by a pair of rails, the sleeve thus having a limited freedom of rotation in the jar equal to the angular spacing of each pair of rails. The plurality of protrusions can be circumferentially distributed around the sleeve periphery in the same number and spacing as the inwardly-directed rails on the jar. In one embodiment, the plurality of protrusions are both circumferentially and axially distributed around the sleeve periphery so as to help center and align the sleeve and jar axes. Each of the protrusions may terminate outwardly in a point, or be wedge-shaped and terminate outwardly in a linear edge. In one version, each of the protrusions is provided on the outer end of a cantilevered arm that has an abrupt edge on one circumferential direction and a smooth edge in the opposite direction so as to provide anti-rotation interference between the sleeve and the jar in one direction but not the other. The protrusions may also comprise a cantilevered leg extending downward from a lower peripheral edge of the sleeve.

Another aspect of the invention is a packaged prosthetic heart valve assembly, comprising a jar having an open end and a closed bottom. A prosthetic heart valve having an inflow end and an outflow end attaches to a valve holder having a mating structure for attachment of a delivery tool. A packaging sleeve sized to fit closely within the jar includes a clip to which the valve holder removably couples. The sleeve further includes at least one pair of protrusions circumferentially distributed around a sleeve periphery in opposing relationship, wherein an exterior diameter defined by the protrusions is larger than an inner diameter of the jar so as to create an anti-rotation interference between the sleeve and the jar and facilitate attachment of the delivery tool to the valve holder.

In one embodiment, the valve holder includes an internally threaded bore for attachment of a threaded male portion of the delivery tool. The plurality of protrusions may be both circumferentially and axially distributed around the sleeve periphery so as to help center and align the sleeve and jar axes. Each of the protrusions may terminates outwardly in a point, or be wedge-shaped and terminate outwardly in a linear edge. In one embodiment, each of the protrusions comprises a cantilevered leg extending downward from a lower peripheral edge of the sleeve. The inner diameter of the jar is defined by the surface of revolution of a plurality of inwardly-directed rails circumferentially distributed around the jar interior that interfere with the sleeve protrusions.

Another packaging sleeve disclosed herein fits closely within a storage jar for holding a prosthetic heart valve. The sleeve is generally tubular and includes tubular wall struts with vents defining spaces therebetween. The sleeve is sized to fit closely within a storage jar and has a clip to which a valve holder removably couples. The sleeve further includes a plurality of generally circumferentially-directed cantilevered arms around a sleeve periphery each defining a tab protruding radially outward through spaces between the tubular wall struts. The tabs are shaped to have an abrupt edge in one circumferential direction and a smooth edge in the opposite direction so as to provide a one-way anti-rotation stop against an inward rail provided in the storage jar. The tubular wall struts can include a series of spaced vertical struts connected by rows of circumferential struts with the vents therebetween.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 1 and 2 are exploded and assembled perspective views of a prosthetic heart valve packaging system including a packaging sleeve and clip holding the prosthetic valve within a storage jar;

FIG. 3 is a top perspective view looking into the storage jar;

FIG. 6 is a perspective view of alternative packaging sleeve having anti-rotation tabs extending outward therefrom;

FIG. 7 is an enlarged top plan view showing engagement between the packaging sleeve of FIG. 6 and a storage jar;

FIG. 8 is a perspective view of a still further alternative packaging sleeve having anti-rotation legs angled outward from a bottom edge;

FIGS. 9A and 9B are perspective and enlarged views of another packaging sleeve having wedge-shaped anti-rotation tabs projecting outward therefrom;

FIG. 10 is perspective view of another packaging sleeve having hemispherical anti-rotation projections around a lower circumference thereof;

FIG. 11 is a perspective view of a packaging sleeve having circumferentially- and axially-spaced wedge-shaped anti-rotation tabs;

FIG. 17 is a perspective exploded view of an alternative prosthetic heart valve holder and sleeve insert assembly similar to FIG. 16 above;

FIG. 18 illustrates the same components after insertion within the storage jar with the sleeve insert removed for clarity and with a delivery handle shown coupled to the valve holder;

FIG. 19 is a top plan view of elements of the packaging system of FIG. 18 illustrating anti-rotation structure therebetween; and FIG. 20 is an alternative heart valve and holder coupled to a packaging sleeve within a storage and shipping jar and showing a tool used for removal of the valve and holder from the jar; and FIGS. 21A and 21B are perspective views of the heart valve and holder without the packaging sleeve and jar to show a process for coupling a leaflet parting member to the holder.

DETAILED DESCRIPTION OF THE PREFERRED EMBODIMENTS

Figure 4A:
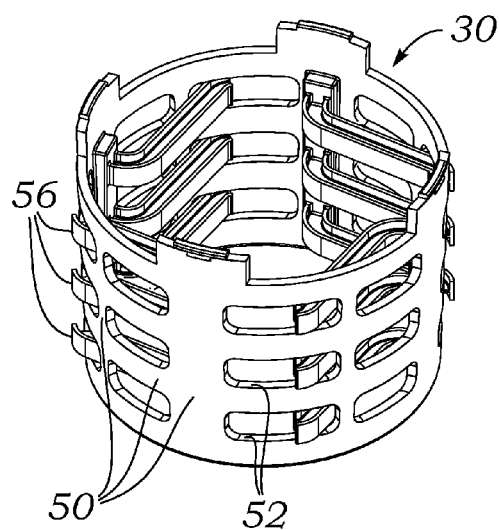
FIGS. 4A-4C are perspective, top plan, and elevational views of an exemplary packaging sleeve having anti-rotation features.

The present invention provides an improved packaging system for prosthetic heart valves that effectively stabilizes the valve within a storage and shipping jar, and permits coupling of a delivery handle to the valve for use in a delivery procedure.

FIG. 1 shows an exploded perspective view of an exemplary prosthetic heart valve packaging system 20. The system 20 includes a jar 22 having a threaded exterior to which a jar lid 24 attaches and provides a good fluid seal. The jar 22 and lid 24 provide a sterile seal for storing prosthetic implants, preferably stored in fluid. However, some implants are stored dry, and the present invention is not limited to wet storage. The jar 22 has a relatively high tubular wall 26 that contacts a resilient seal (not shown) provided within the jar lid 24. A generally tubular packaging sleeve 30 fits closely within the tubular wall 26 of the jar 22. The packaging sleeve has a generally tubular wall structure 32 and a plurality of upper mounting tabs 33 that fit within correspondingly-sized and spaced mounting apertures 34 in a disk-shaped clip 36. The clip 36 includes structure thereon to which a prosthetic heart valve 40 mounts. More specifically, the heart valve 40 mounts to a valve holder 42 that attaches to or includes a handle engagement mechanism (not shown) that is held by the clip 36. In the illustrated embodiment, the clip 36 and handle engagement mechanism operate in coordination with a leaflet constrictor 44 which is described briefly below. The assembly of the prosthetic heart valve 40 mounted on the clip 36 fits over the top of the packaging sleeve 30 within the jar 22. The assembled packaging system 20 is seen in FIG. 2.

FIG. 3 is a top perspective view looking into the storage jar 22 and illustrates a plurality of axial anti-rotation rails 46 formed on an inner surface of the tubular wall 26. The particular configuration and number of anti-rotation rails 46 may vary, and preferably mirrors the number of anti-rotation tabs provided on the packaging sleeve 30, as will be described below. Preferably, however, there are at least two rails 46 extending inward from the tubular wall 26 at diametrically opposed locations which define an inner diameter smaller than the inner diameter of the tubular jar wall.

The packaging sleeve 30 disclosed herein include more than one part; specifically, the generally tubular wall structure 32 and the clip 36. However, it should be understood that a packaging sleeve formed of a single, unitary component, preferably molded plastic, is entirely possible and encompassed by the present application.

The particular prosthetic heart valve 40 disclosed includes bioprosthetic leaflets which are typically stored in a preservative solution, such as glutaraldehyde. Therefore the packaging sleeve 30 fits closely within the fluid tight shipping jar 22 which is then sealed with the lid 24. However, certain features of the exemplary heart valve and delivery system may be adapted for valves that do not require storage in a fluid preservative, and instead may use a dry sterile jar. The invention should therefore not be considered limited to a valve packaging system having a fluid preservative.

The illustrated prosthetic heart valve 40 may take a variety of forms, but preferably includes a cloth-covered wireform that follows an undulating path around the periphery of the valve with alternating cusps (not numbered) and commissure posts. A plurality of flexible leaflets extend across a generally circular orifice defined within the prosthetic valve 40, each of which receives peripheral support along the wireform, in particular by two adjacent commissure posts. An annular, preferably contoured, sewing ring circumscribes the valve 40 to provide structure for suturing the heart valve into a diseased annulus of a patient. However, it should be understood that various constructions of valves are available, including those with flexible leaflets and those with rigid leaflets, or even a ball and cage arrangement. The leaflets may be bioprosthetic, synthetic, metallic, or other suitable expedients. The present application should not be considered limited to any one particular prosthetic heart valve.

FIG. 1 illustrates a portion of an exemplary heart valve holder 42 used with the packaging sleeve 30, with the rest being substantially occluded by the clip 36. Though not shown, the holder 42 desirably comprises a proximal tubular hub forming a central portion of the holder and three legs circumferentially equidistantly spaced and projecting radially outward therefrom (one of which can be seen). The holder legs correspond to a plurality, typically three, valve commissures 48 that project in an outflow direction. Per convention, the holder 42 has a series of through holes in the legs permitting connecting sutures to be passed through fabric in the prosthetic valve 40 and across a proximal cutting guide in each leg. As is known in the art, severing a middle length of any sutures that connect to the holder 42 and pass through the valve permits the holder to be pulled free from the valve when desired.

As mentioned, the valve holder 42 attaches to a handle engagement mechanism (not shown) held by the clip 36 which contain between them a leaflet constrictor 44. The constrictor 44 will not be described in detail, but functions to pull the valve commissures 48 inward prior to a delivery procedure. This is advantageous for mitral valves that are advanced through the anatomical passages with the valve commissures 48 in a leading position, susceptible to becoming entangled with an array of anchoring sutures. However, as mentioned above, the present application also pertains to mitral valve packaging systems that do not have commissure constriction mechanisms, and also to aortic valve packaging systems where the holder attaches to the tips of the valve commissures rather than to an inflow sewing ring.

The exemplary holder 42 further includes a threaded bore or other connector (not shown) that permit it to couple with a delivery system, such as a delivery handle. Because the holder 42 is located toward the top of the package within the jar 22, and the holder 42 is exposed to the open mouth of the jar, a delivery handle can easily be inserted by a technician to the jar and couple to the holder. In the case of a threaded bore, the handle is simply screwed into the holder. In the case of a bayonet, snap lock or other such connector, the technician inserts and turns the handle to lock it into the holder. Examples of such handle/holder connections are shown in U.S. Pat. No. 4,865,600 to Carpentier, et al., U.S. Pat. No. 6,964,682 to Nguyen, et al., and U.S. Pat. No. 6,966,925 to Stobie, all expressly incorporated herein by reference. In each of these configurations, the valve holder must be held stationary within the jar while screwing in the handle, otherwise it will rotate.

FIGS. 1 and 4A-4C illustrate an exemplary packaging sleeve 30 having a generally tubular wall structure 32 defined by a plurality of tubular wall struts 50. In the illustrated embodiment, the wall struts 50 include a series of spaced vertical struts connected by rows of circumferential struts with vents 52 defining spaces therebetween. The exact arrangement of the wall struts 50 may vary, as long as the number and size of vents 52 permits good fluid flow in and around the packaging sleeve 30 so that the liquid sterilant distributes evenly through the jar 22. The illustrated embodiment has four large vertical struts spaced at 90° around the tubular wall 32 with four horizontal rows of circumferential struts therebetween, and four thinner vertical rows of struts connecting the horizontal rows. The upper mounting tabs 33 project from each of the four large vertical struts. There are thus a total of twenty-four vents 52 around the perimeter of the packaging sleeve 30. Note the top and bottom of the sleeve 30 are open.

Figure 4B:
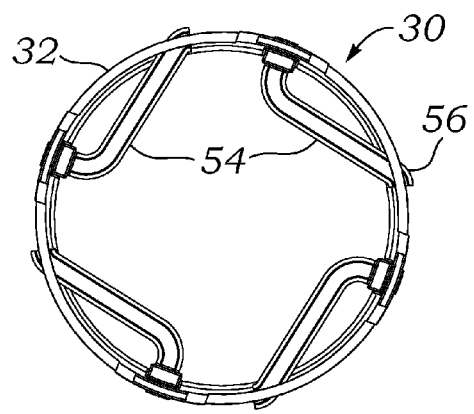
Figure 4C:
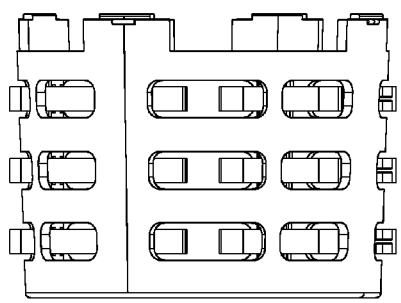

The packaging sleeve 30 further includes a plurality of generally circumferentially-directed cantilevered arms 54 around the sleeve periphery. More specifically, each of the arms 54 extends inward from one of the large vertical struts 50 and curves in a circumferential direction so as to extend generally along the inside of the tubular wall structure 32. When viewed from above, as seen in FIG. 4B, the cantilevered arms 54 extend in a clockwise (CW) direction. In the illustrated embodiment, there are 12 arms, three vertically spaced from each other at 90° intervals. However, it will be understood that as few as two such cantilevered arms 54 may be utilized. Each arm 54 defines a tab 56 protruding radially outward through the vents 52 between the tubular wall struts 50. The tabs 56 are shaped to have an abrupt edge in one circumferential direction and a smooth edge in the opposite direction so as to provide a one-way anti-rotation stop against the inward rails 46 provided in the storage jar. The distinction between abrupt and smooth is analogous to that between a sharp and a curved corner or, in other words, between a corner at the intersection of (discontinuity between) two surfaces which are at different angles (preferably forming a right or acute angle) and a corner which has either no distinct surface intersection or defines an obtuse angle of at least 135°.

Figure 5A:
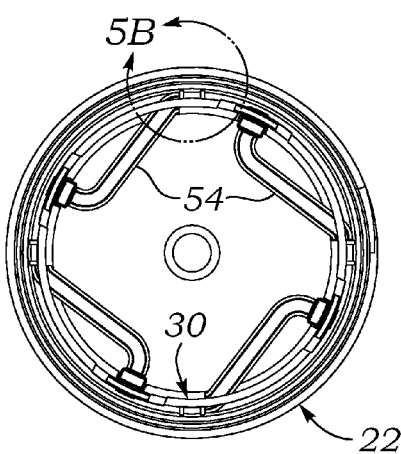
FIGS. 5A and 5B are top plan and enlarged views thereof showing anti-rotation engagement between the packaging sleeve and storage jar.
Figure 5B:
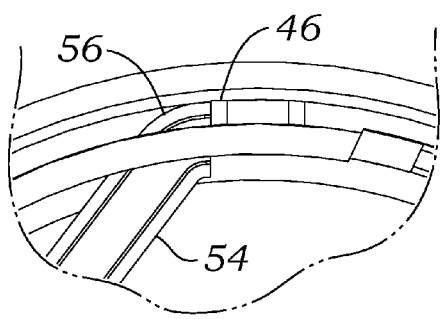

FIGS. 5A and 5B show the exemplary anti-rotation engagement between the packaging sleeve 30 and the storage jar 22. Specifically, each of the tabs 56 projects outward through a vent 52 into engagement with one or more of the rails 46. The abrupt edge of the tab 56 faces to the right, while the smooth edge faces to the left. The reader will understand, therefore, that CW rotation of the sleeve 30 will be prevented by the engagement of the abrupt edges of the tabs 56 against the rails 46. On the other hand, counter-clockwise (CCW) location of the sleeve 30 is possible by virtue of the smooth edges of the tabs 56 camming over the rails 46 permitted by the flexible, cantilevered construction of the arms 54. The reader will understand that the illustrated configuration is designed for right-handed threading on the handle and valve holder 42, which means that the handle will be screwed onto the holder in a CW direction. Of course, this configuration could just as easily be left-handed, in which case the arms 54 would be directed in the opposite, or CCW, direction.

When threading a delivery handle onto a valve holder 42 secured within the sleeve 30 the sleeve rotation is limited to the angular distance between any of the tabs 56 and the next adjacent jar rail 46. The extent of rotation permitted is therefore approximately equal to the angular spacing between the pairs of axial jar rails 46, which is preferably between about 80-90°, more preferably less than or equal to about 90°. This anti-rotation feature restricts the rotational movement of the valve during distribution to customers as well as facilitates the attachment of a deployment handle to the valve. It should be understood that a minimum of one rail 46 and one sleeve tab 56 is necessary to limit rotation of the sleeve in the jar, which would mean the sleeve could potentially rotate almost 360° before stopping. Desirably, however, there are at least two pairs of rails/tabs, limiting rotation to almost 180°, and more particularly at least three pairs of rails/tabs. In general it is desirable to have the same number of jar rails 46 and sleeve tabs 56 at symmetric placements, which obviates the need for placing the sleeve into the jar in a specific orientation.

Placing the interacting tabs 56 and rails 46 on the radial walls of the two parts permits the technician to engage the tool to the valve holder in various orientations of the jar, even inverted, which was not the case with earlier designs with the anti-rotation feature on the bottom of the jar. Furthermore, the anti-rotation cooperation between the jar 22 and sleeve 30 provides a positive stop to the handle-to-holder assembly procedure, in that the user feels a threaded handle, e.g., bottoming out in the threaded bore of the holder 42.

FIG. 6 illustrates an alternative packaging sleeve 60 having fixed anti-rotation tabs 62 extending outward therefrom. As in the previous embodiment, the sleeve 60 includes a tubular body comprising a plurality (preferably four) vertical struts 64 joined by three rows of horizontal struts 66. Vents 68 are provided between the struts or good sterilant flow within the jar. In the illustrated embodiment, there are twelve anti-rotation tabs 62; three each on the three horizontal struts 66 extending between adjacent vertical struts 64. Upper clip mounting tabs 70 are provided on the top end of each of the four vertical struts 64 for receiving apertures in a valve holder mounting clip, such as the clip 36 described above.

FIG. 7 is an enlarged top plan view showing engagement between the packaging sleeve 60 and the storage jar 22 having rails 46. In this embodiment, the anti-rotation tabs 62 fit between two adjacent parallel rails 46 so that there is no relative rotation between the sleeve 60 and the jar 22. This configuration accommodates both left- and right-handed threading between a delivery handle and a valve holder secured by the sleeve 60. Of course, with this arrangement some additional care is required when assembling the valve packaging system to align the tabs 62 between the parallel pairs of rails 46. Another option is to provide a multitude of rails 46 spaced close together as in FIG. 7 so that the tabs 62 fit between two adjacent rails in any relative jar/sleeve orientation. In such an embodiment, no rotation of the sleeve 60 in the jar 22 would occur and it would not matter what location the sleeve is inserted into the jar, thus facilitating the assembly process. Many other variations of rail and tab combinations are possible, as will be understood.

FIG. 8 shows a still further alternative packaging sleeve 80 having anti-rotation legs 82 angled outward from a bottom edge 84. The sleeve 80 primarily comprises a tubular structure formed by vertical and horizontal struts 86, with upstanding posts 88 terminating in clip mounting tabs 90. The outer diameter of the tubular structure is slightly smaller than the inner diameter of a complementary storage jar, but an outer diameter defined by the anti-rotation legs 82 is slightly larger than the jar ID. This creates a frictional interference fit between the anti-rotation legs 82 and the inside of the jar. The legs 82 are cantilevered about the bottom edge 84, and provide sufficient force to resist rotation of the sleeve 80 when attaching a delivery handle to a valve holder secured to the sleeve. Moreover, while assembling a delivery handle to a valve holder, the user presses the sleeve 80 down into the jar, further spreading the flared legs 82 and increasing resistance to rotation. However, the interference between the legs 82 and the jar, and resistance to relative movement, is not so much that assembly of the sleeve 80 into jar is rendered difficult. The sleeve 80 is press-fit into the jar, and the frictional interference between the bottom edge of the legs 82 and the jar eliminate all sleeve rotational and vertical movement, within a certain force threshold which is less than the torque imparted by threading a delivery handle onto the holder. The press-fit configuration means that the sleeve 80 will remain in the jar while the valve/holder assembly attached to the clip is removed once the handle is attached.

FIGS. 9A and 9B illustrate another packaging sleeve 100 having wedge-shaped anti-rotation friction-inducing tabs 102 projecting outward therefrom. The tubular frame of the sleeve 100 is similar to those described above, and the tabs 102 project outward from a lower end of the sleeve on each of the four vertical struts 104. The diameter defined by the tabs 102 is larger than an ID of the jar, creating a frictional interference therebetween. The wedge shape of the tabs 102 creates a linear edge contact (nearly a point contact) with the inner wall of the jar which resists rotation of the sleeve 100 in the jar and helps maximize fluid flow in and around the sleeve 100.

FIG. 10 shows a packaging sleeve 110 similar to the sleeve 100 in FIG. 9A, but having hemispherical anti-rotation projections 112 around a lower circumference thereof. Again, the point contact of the hemispherical projections 112 facilitates fluid flow around the outside of the sleeve 110. Furthermore, in contrast to the sleeve 100, the anti-rotation projections 112 are positioned midway along a lower horizontal strut 114, rather than on the vertical struts 116.

FIG. 11 illustrates a still further packaging sleeve 120 having circumferentially- and axially-spaced wedge-shaped anti-rotation tabs 122. A lower row of tabs 122a extends around the circumference of the sleeve 120 aligned with vertical struts 124 as well as in the middle of horizontal struts 126. Since there are four vertical struts 124, there are eight tabs 122a in the lower row. A second row of anti-rotation tabs 122b approximately midway up the sleeve 120 includes one at each vertical strut 124; for a total of four. The circumferentially and axially spaced tabs 122a, 122b insure that the sleeve 120 remains centered and vertical within the jar. This centering helps with insertion of other components into the jar and onto the sleeve 120, and makes it easier for the user to remove the device without any component snags. Again, for positional stability a minimum number of tabs 122 in any one row is three.

Figure 12:
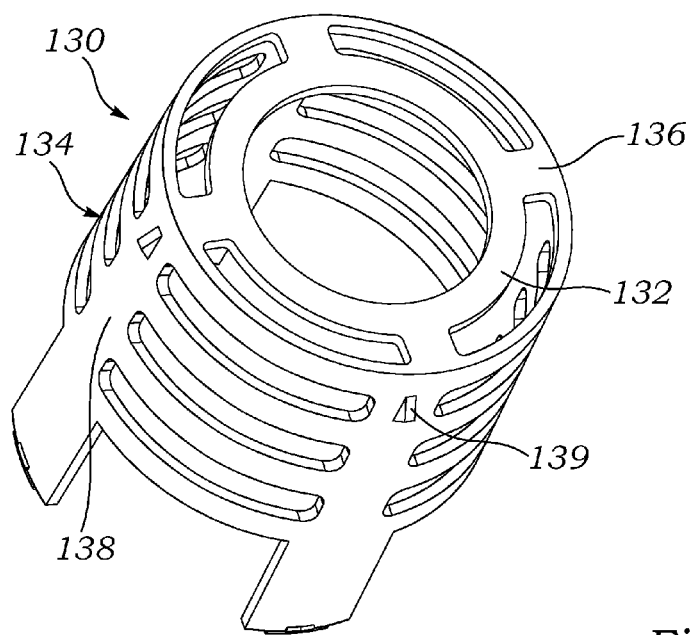
FIG. 12 is a bottom perspective view of a packaging sleeve similar to that shown in FIG. 9A and having a reinforcing ring across a bottom surface thereof.
Figure 13:
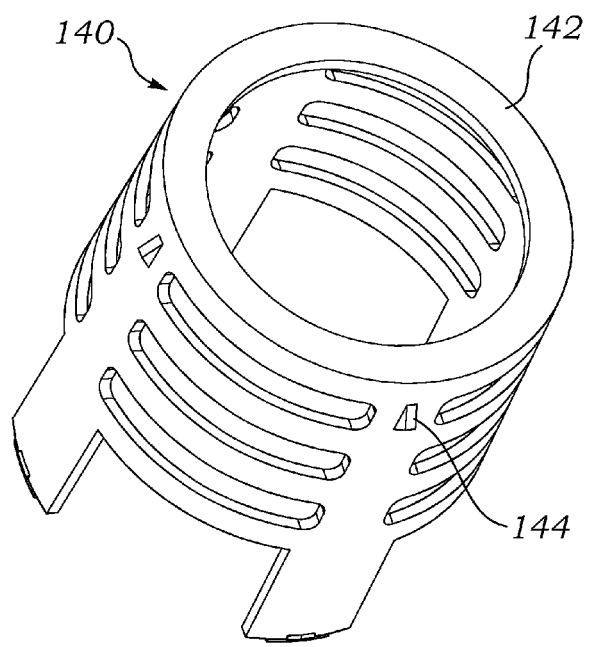
FIG. 13 is a bottom perspective view of another packaging sleeve having a reinforcing circle along a bottom edge thereof.

FIGS. 12 and 13 illustrate packaging sleeves 130, 140 that have reinforcing structure along bottom edges thereof. When stored for a long period of time the polymers used to form the various sleeves described herein may be susceptible of material creep, in which the sleeve shrinks, or in the press-fit embodiments, assumes a smaller diameter if subjected to constant inward pressure from the surrounding jar.

FIG. 12 illustrates a sleeve 130 similar to that shown in FIG. 9A, but which further incorporates a reinforcing ring 132 across the bottom surface thereof. The ring 132 connects to the outer tubular body 134 by a plurality of radial arms 136. In the illustrated embodiment, there are four radial arms 136 aligned with four vertical struts 138. Furthermore, wedge-shaped anti-rotation tabs 139 are located along the vertical struts 138. The reinforcing ring 132 and radial arms 136 thus provide stiffness to the bottom of the sleeve 130 and resist any material creep at a location, which maintains good contact between the anti-rotation tabs 139 and jar, even over long periods of time.

FIG. 13 illustrates an alternative sleeve 140 in which the reinforcement on the bottom of the sleeve comprises a flat circular flange 142. Again, this reinforcement ring maintains contact between anti-rotation tabs 144 and the inside wall of jar.

Figure 14:
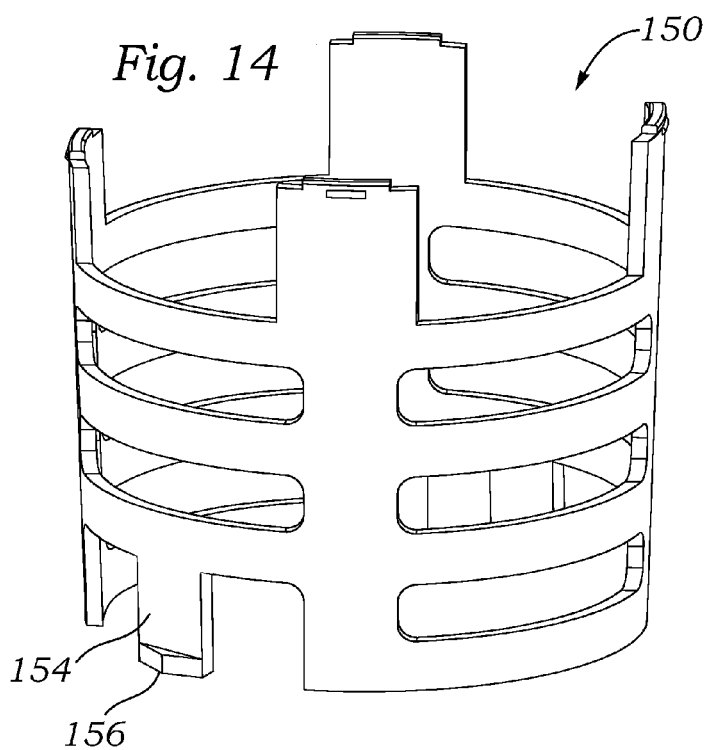
FIGS. 14 and 15 show alternative packaging sleeves having, respectively, two and four cantilevered lower legs with wedge-shaped anti-rotation tabs thereon.
Figure 15:
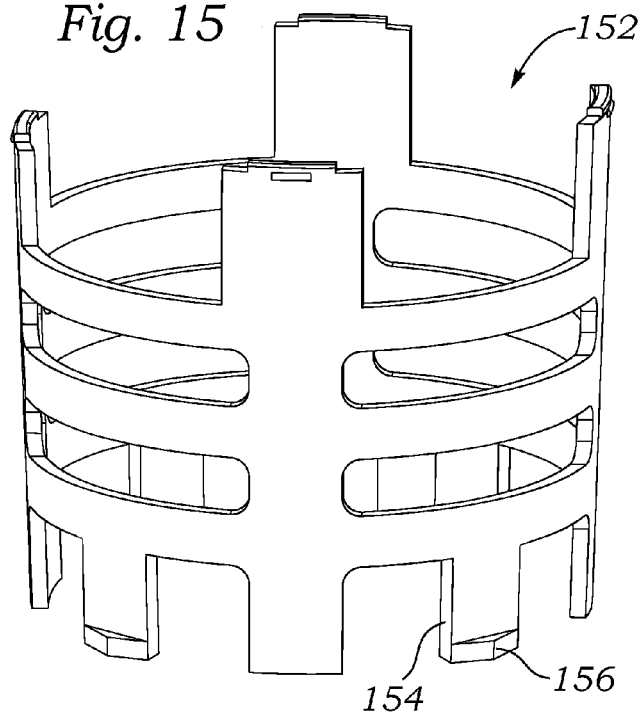

FIGS. 14 and 15 show alternative packaging sleeves 150, 152 having, respectively, two and four cantilevered lower legs 154 with wedge-shaped anti-rotation tabs 156 thereon. The geometry of the tabs 156 may be modified to be other than wedge-shaped, such as hemispheric, saw-bladed, straight rectangular, etc. The legs 154 are capable of significant flexing, and therefore the magnitude of interference between the exterior diameter defined by the tabs 156 and the inner diameter of the jar can be increased, without substantially increasing the difficulty of inserting the sleeve into the jar. Furthermore, the level of interference is influenced, and can therefore be controlled, by the stiffness of the legs 154 in conjunction with the shape of the tabs 156.

Figure 16:
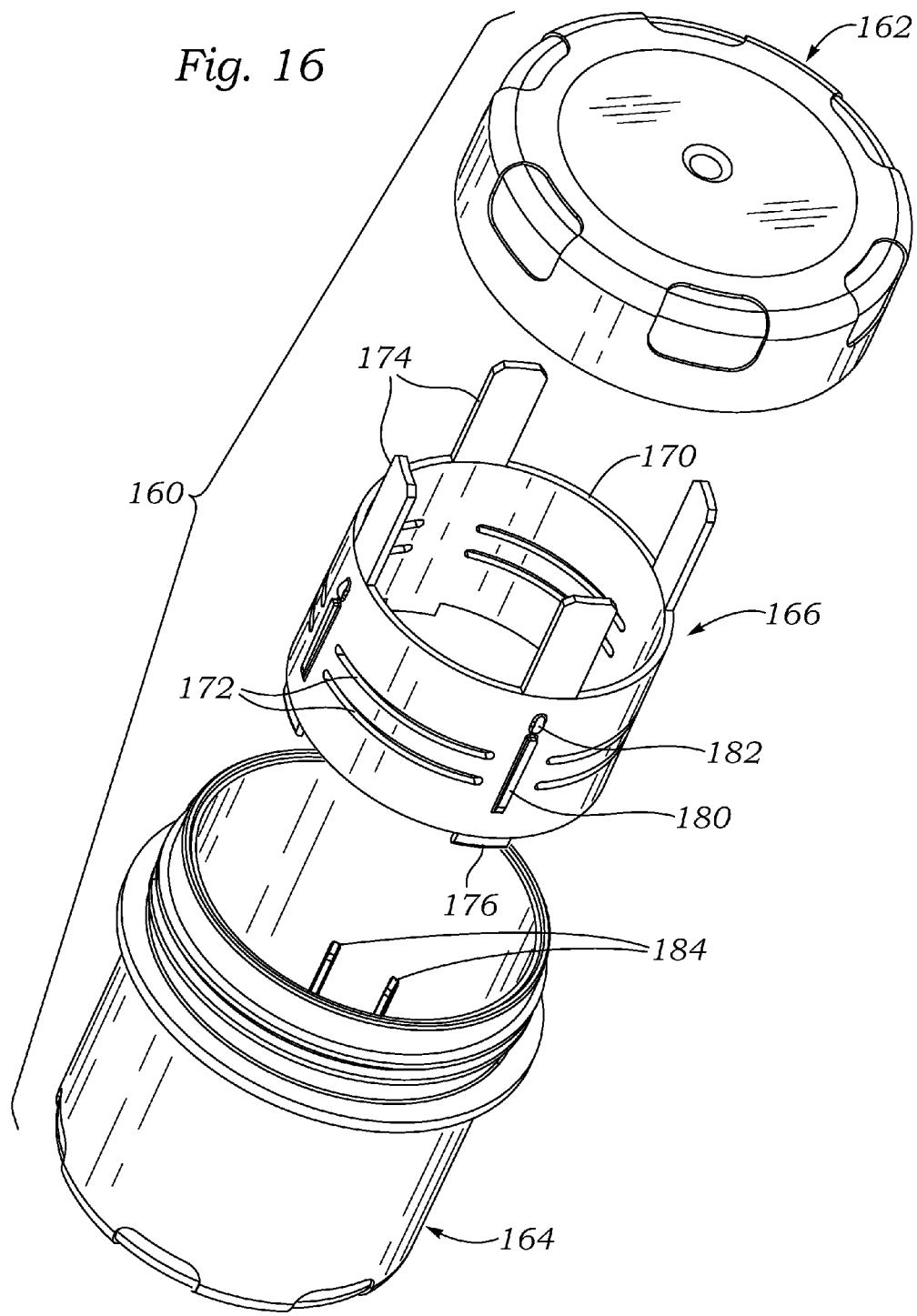
FIG. 16 is a perspective view of a further exemplary prosthetic heart valve packaging system having a short lid.

FIG. 16 is a perspective view of a further exemplary prosthetic heart valve packaging system 160 having a short lid 162 arranged to seal onto a jar 164 that receives a packaging sleeve 166 therein. The sleeve 166 includes a substantially solid tubular body 170 having two rows of interrupted horizontal vents 172 to permit sterilant flow within the jar. Four vertical struts 174 project up from the upper rim of the tubular body 170 for coupling to a valve holder mounting clip, such as the clip 36 described above. Short feet 176 extend downward from the body 170 to raise the lower rim thereof above the jar floor.

The packaging sleeve 166 has a plurality of anti-rotation friction-inducing ribs 180 and bumps 182 projecting outward from the tubular body 170. In the illustrated embodiment, there are four anti-rotation ribs 180 and four bumps 182, with vertically-aligned pairs of one rail and one bump evenly spaced around the tubular body 170. Preferably, the pairs of ribs 180 and bumps 182 align with the vertical struts 174 and feet 176. The diameter defined by the surface of revolution of the ribs 180 and bumps 182 is larger than the ID of the jar 164, creating a frictional interference therebetween. More preferably, vertical rails 184 are provided within the jar 164 to positively interfere with rotation of the ribs 180 and bumps 182.

Another potential configuration features a packaging sleeve for mounting a valve holder that is built into the jar. That is, the jar may be formed to receive the valve holder (or an intermediary such as the clip 36 in FIG. 1) in a stable and non-rotational position. Although an integrated jar/sleeve arrangement such as that is contemplated, manufacturing difficulties favor separately molded jar and sleeve components. Moreover, some surgeons may prefer the surrounding walls of the sleeve to protect the valve as it is removed from the jar.

FIGS. 17 and 18 show an alternative prosthetic heart valve 190 on its holder 192 and within the sleeve 166 that fits within and engages the packaging and storage jar 164, as in FIG. 16. FIG. 18 shows the components after insertion within the storage jar 164 the sleeve 166 removed for clarity and with a delivery handle 194 coupled to the valve holder. The holder 192 includes three outwardly directed legs 196 that couple to a sewing ring 198 on the prosthetic heart valve 190 via sutures 200. The holder 192 snaps onto a flat disk 201 that extends outward to the sleeve 166 and features a series of slots 202 that mate with the upstanding struts 174 on the sleeve. The assembly of the disk 201 and sleeve 166 supports and suspends the valve 190 within the storage jar 164 to prevent it moving around therein during shipping and handling. This arrangement of holder 192 and heart valve 190 is shown in U.S. Pat. No. 6,966,925, and is similar to pericardial bioprosthetic heart valves sold under the Magna® name by Edwards Lifesciences of Irvine, Calif.

FIG. 19 is a top plan view of elements of the packaging system of FIG. 18 illustrating anti-rotation structure therebetween. Namely, as seen above in FIG. 16, packaging sleeve 166 has the anti-rotation ribs 180 and bumps 182 projecting outward from the tubular body 170. The diameter defined by the surface of revolution of the ribs 180 and bumps 182 is larger than that of the rails 184 projecting inward from the inside wall of the jar 164, creating an interference therebetween. Preferably there are four sets of ribs 180 and bumps 182 distributed evenly at 90° intervals, and four pairs of rails 184 also evenly distributed around the inside of the jar 164. Each pair of rails 184 is spaced apart a slight amount so that it is easy for an assembler to place the sleeve 166 into the jar 164 with each set of the ribs 180 and bumps 182 flanked by a pair of rails 184 as shown. This arrangement permits a small amount of rotational freedom of the sleeve 166 relative to the jar 164, preferably no more than about 30°. That is, each pair of rails 184 is circumferentially spaced apart by up to about 30°, preferably between 15-30°. Of course, a similar limited freedom of movement can be attained with more or less than four sets of the mating ribs/bumps and rails, such as three sets spaced 120° apart.

With reference back to FIG. 18, the delivery handle 194 includes a male threaded end (not shown) that screws into a female threaded bore 204 on the top end of a holder post 206. Because of the interference between the sleeve ribs 180 and bumps 182 and the jar rails 184, the technician can easily screw the handle 194 into the holder post 206 while holding the jar 164 at various angles. At a predetermined rotation of the handle 194 relative to the holder post 206, the mating threads tighten and further rotation causes rotation of the holder post 206 relative to the legs 196 and a central hub structure. As seen in FIG. 17, the post 206 has an axial key 208 that prevents downward movement of the post until it aligns with a keyway 210. Rotation of the delivery handle 194 after bottoming out into the post 206 thus moves the key 208 over the keyway 210, which permits the user to push the post downward, as indicated in FIG. 18. The lower end 212 of the post 206 contacts and tensions portions of the sutures 200 that traverse across the outflow end of the heart valve 190, pulling valve commissures 214 inward. Again, this advantageous feature is disclosed in U.S. Pat. No. 6,966,925.

FIG. 20 shows an alternative heart valve 220 and holder 222 coupled to a packaging sleeve 224 within a storage and shipping jar 226. An elongated shaft 246 used for removing the heart valve 220 from within the jar 226 is shown descending toward the jar opening. FIGS. 21A-21B show several steps in a process for coupling a leaflet parting member 240 of a valve delivery system to the holder 222, as better explained in co-pending U.S. application Ser. No. 12/969,238, the contents of which are expressly incorporated herein by reference.

The parting member 240 comprises a short tubular member having a stepped diameter with an externally-threaded narrower distal portion 242 and a wider proximal portion 244 with no threads. The parting member 240 couples to the elongated shaft 246 via mating threading, a snap lock, bayonet lock, a simple interference fit, or other quick-release coupling.

As depicted in FIG. 20, the elongated shaft 246 has sufficient length to deliver the parting member 240 on its distal end into the jar 226 and through the valve 220 to the holder 222. FIGS. 21A and 21B illustrate the coupling operation with the sleeve 224 and jar 226 removed for clarity. It should be understood that although the parting member 240 is desirably coupled to the holder 222 while it remains in the jar 226, the entire assembly of the packaging sleeve 224 and valve/holder may be first removed from the jar 226 by hand or forceps.

However, the reader can assume that the steps shown in FIGS. 21A and 21B are performed with the assembly still in the jar 226.

A technician advances the parting member 240 on the end of the shaft 246 through a conical coupling stent 232 of the prosthetic valve 220. Since flexible valve leaflets 236 are angled inward from the inflow to the outflow direction (downward in the drawings), the parting member 240 easily passes therebetween in the same direction, in the process displacing the leaflets outward. Ultimately, the technician advances the parting member 240 far enough into contact with the holder 222, and screws the external threads on the distal portion 242 into internal threads on a tubular hub 250 of the holder. Interference between outwardly-directed ribs 252 or other structure on the packaging sleeve 224 with inward rails 254 in the jar 226 prevents rotation of the holder (beyond a short angular rotation of up to 30°) relative to the sleeve during this engagement. The storage jar 226 may be configured similarly to the jar 22 of FIG. 3 described above having similar rails 46. The final position of the parting member 240 coupled to the holder 222 is shown in FIG. 21B, with a length of the threaded distal portion 242 projecting from the hub 250 of the holder.

While the invention has been described in its preferred embodiments, it is to be understood that the words which have been used are words of description and not of limitation. Therefore, changes may be made within the appended claims without departing from the true scope of the invention.

What is claimed is:

1. A packaged prosthetic heart valve assembly, comprising:
a jar having an open end and a closed bottom, and a plurality of inwardly-directed rails circumferentially distributed around the jar interior;
a prosthetic heart valve having an inflow end and an outflow end;
a valve holder attached to one end of the valve; and
a generally tubular packaging sleeve having a tubular wall sized to fit closely within the jar and having structure to which the valve holder removably couples so that the heart valve is restrained from gross movement within the jar, the sleeve further including a plurality of radially-outwardly projecting protrusions in the tubular wall circumferentially distributed around a sleeve periphery, there being at least two differently configured and axially-spaced protrusions at each circumferential location, wherein an exterior diameter defined by the protrusions is larger than an inner diameter defined by the rails so as to create an anti-rotation interference between the sleeve and the jar to limit rotation of the sleeve while in the jar, the sleeve further including vents in the tubular wall between each circumferential location at which there are protrusions.

2. The assembly of claim 1, wherein the plurality of protrusions are evenly circumferentially distributed around the sleeve periphery, and there are two inwardly-directed rails on the jar for every circumferential location at which there are protrusions on the sleeve so that each protrusion may be flanked by a pair of rails, the sleeve thus having a limited freedom of rotation in the jar equal to the angular spacing of each pair of rails.

3. The assembly of claim 1, wherein there are the same number of circumferential locations at which there are protrusions as the inwardly-directed rails on the jar.

4. The assembly of claim 1, wherein the protrusions at each circumferential location at which there are protrusions comprise a linear rib and a bump that is axially shorter than the linear rib.

5. A packaged prosthetic heart valve assembly, comprising:
a cylindrical jar having an open end and a closed bottom, and a cylindrical inner wall;
a prosthetic heart valve having an inflow end and an outflow end;
a valve holder attached to one end of the valve and including mating structure for attachment of a delivery tool; and
a generally tubular packaging sleeve having a tubular wall sized to fit closely within the jar and having a clip to which the valve holder removably couples, the sleeve further including at least two pairs of protrusions in the tubular wall circumferentially distributed around a sleeve periphery in opposing relationship, wherein the two protrusions in each pair are differently configured, an exterior diameter defined by the protrusions being larger than an inner diameter of the inner wall of the jar so as to create an anti-rotation interference between the sleeve and the jar and facilitate attachment of the delivery tool to the valve holder.

6. The assembly of claim 5, wherein the valve holder includes an internally threaded bore for attachment of a threaded male portion of the delivery tool.

7. The assembly of claim 5, wherein the plurality of protrusions are both circumferentially and axially distributed around the sleeve periphery so as to help center and align the sleeve and jar axes.

8. A packaged prosthetic heart valve assembly, comprising:
a jar having an open end and a closed bottom, and a plurality of inwardly-directed rails circumferentially distributed around the jar interior;
a prosthetic heart valve having an inflow end and an outflow end;
a valve holder attached to one end of the valve; and
a generally tubular packaging sleeve having a tubular wall sized to fit closely within the jar and having structure to which the valve holder removably couples so that the heart valve is restrained from gross movement within the jar, the tubular sleeve defining a lower rim and further including a plurality of feet extending downward from the rim which contact the bottom of the jar when positioned therein so as to raise the lower rim above the bottom and permit fluid flow therebetween, the sleeve further including a plurality of vertically-oriented anti-rotation ribs in the tubular wall circumferentially distributed around and extending outward from a sleeve periphery and located above the lower rim, there being at least two differently configured and axially spaced ribs at multiple circumferential locations, wherein an exterior diameter defined by the ribs is larger than an inner diameter defined by the rails so as to create an anti-rotation interference between the sleeve and the jar to limit rotation of the sleeve while in the jar, and wherein there are two inwardly-directed rails on the jar for every rib on the sleeve so that each rib may be flanked by a pair of rails, the sleeve thus having a limited freedom of rotation in the jar equal to the angular spacing of each pair of rails, the sleeve further including vents in the tubular wall between each circumferential location at which there are protrusions.

9. The packaging sleeve of claim 8, further including a plurality of anti-rotation bumps extending outward from the sleeve periphery, one bump for each rib and each bump is axially aligned with an associated rib.

10. The packaging sleeve of claim 8, wherein each pair of two inwardly-directed rails on the jar is circumferentially spaced apart by between about 15-30°.

11. The packaging sleeve of claim 8, further including a plurality of vertical struts circumferentially distributed around the tubular packaging sleeve and projecting upward.

12. The packaging sleeve of claim 8, wherein the valve holder snaps onto a flat disk that extends outward and is supported by the tubular packaging sleeve, and wherein the valve holder includes three legs that couple to a sewing ring on the prosthetic heart valve via sutures, the valve holder further including a female threaded bore on the top end of a holder post that is rotatable relative to the legs and a central hub structure, and the post has an axial key that prevents downward movement of the post until it aligns with a keyway in the central hub structure, and wherein rotation of a delivery handle after bottoming out into the female threaded bore of the post thus rotates the post such that the key aligns with the keyway to permit the post to move axially.

\* \* \* \* \*